(12) United States Patent
Pi et al.

(10) Patent No.: US 12,185,475 B2
(45) Date of Patent: Dec. 31, 2024

(54) ELECTRONIC DEVICE AND METHOD OF MANUFACTURING THE SAME

(71) Applicant: Advanced Semiconductor Engineering, Inc., Kaohsiung (TW)

(72) Inventors: Tun-Ching Pi, Kaohsiung (TW); Ming-Hung Chen, Kaohsiung (TW)

(73) Assignee: ADVANCED SEMICONDUCTOR ENGINEERING, INC., Kaohsiung (TW)

( * ) Notice: Subject to any disclaimer, the term of this patent is extended or adjusted under 35 U.S.C. 154(b) by 0 days.

(21) Appl. No.: 17/239,475

(22) Filed: Apr. 23, 2021

(65) Prior Publication Data

US 2022/0346239 A1 Oct. 27, 2022

(51) Int. Cl.
| | | |
|---|---|---|
| H05K 1/02 | (2006.01) | |
| A61B 5/00 | (2006.01) | |
| G06F 1/16 | (2006.01) | |
| H05K 3/34 | (2006.01) | |

(52) U.S. Cl.
CPC .......... *H05K 3/341* (2013.01); *A61B 5/6802* (2013.01); *G06F 1/163* (2013.01); *H05K 1/0201* (2013.01)

(58) Field of Classification Search
CPC .... H05K 3/341; H05K 1/0201; A61B 5/6802; G06F 1/163
USPC ........................................................ 174/260
See application file for complete search history.

(56) References Cited

U.S. PATENT DOCUMENTS

| | | | | |
|---|---|---|---|---|
| 5,898,161 A * | 4/1999 | DeVita | ................... | G06F 1/1666 |
| | | | | 235/472.01 |
| 6,619,835 B2 * | 9/2003 | Kita | ...................... | A44C 5/0015 |
| | | | | 368/282 |
| 8,319,601 B2 * | 11/2012 | Gelman | ................... | G07C 9/28 |
| | | | | 340/5.2 |
| 8,903,671 B2 * | 12/2014 | Park | ....................... | A61B 5/021 |
| | | | | 702/104 |
| 8,920,332 B2 * | 12/2014 | Hong | ................. | A61B 5/02438 |
| | | | | 600/483 |
| 9,583,256 B2 * | 2/2017 | Lapetina | .................. | H01F 27/36 |
| 9,978,693 B2 * | 5/2018 | Jeong | .................... | H01L 23/552 |
| 11,224,132 B2 * | 1/2022 | Chen | .................... | H05K 9/0022 |
| 2011/0067904 A1 * | 3/2011 | Aoyama | ............... | H05K 3/4069 |
| | | | | 174/254 |
| 2015/0138699 A1 * | 5/2015 | Yamazaki | ................ | G06F 1/163 |
| | | | | 361/679.03 |
| 2015/0264798 A1 * | 9/2015 | Stanley | .................. | H05K 3/284 |
| | | | | 361/749 |
| 2015/0309535 A1 * | 10/2015 | Connor | ................ | A61B 5/1477 |
| | | | | 361/679.03 |
| 2015/0331447 A1 * | 11/2015 | Hasegawa | ............ | H05K 1/0281 |
| | | | | 361/679.03 |

(Continued)

*Primary Examiner* — Anatoly Vortman
(74) *Attorney, Agent, or Firm* — FOLEY & LARDNER LLP

(57) ABSTRACT

The present disclosure provides an electronic device and method of manufacturing the same. The electronic device includes a first region, a second region, an electronic component, and a first sensing element. The second region is adjacent to the first region. The first region has a first pliability. The second region has a second pliability. The second pliability is greater than the first pliability. The electronic component is disposed at the first region. The first sensing element is disposed at the second region and electrically connected to the electronic component.

19 Claims, 15 Drawing Sheets

(56) References Cited

U.S. PATENT DOCUMENTS

| | | | |
|---|---|---|---|
| 2015/0338879 A1* | 11/2015 | Hiramoto | G06F 1/163 |
| | | | 361/749 |
| 2016/0014888 A1* | 1/2016 | Xia | H05K 1/189 |
| | | | 174/254 |
| 2016/0125709 A1* | 5/2016 | Thaler | B06B 1/0207 |
| | | | 340/407.1 |
| 2017/0235341 A1* | 8/2017 | Huitema | G04G 17/08 |
| | | | 361/679.03 |
| 2018/0307314 A1* | 10/2018 | Connor | A61B 5/1123 |
| 2019/0059152 A1* | 2/2019 | Boozer | H05K 5/064 |
| 2021/0076510 A1* | 3/2021 | Chen | H05K 5/065 |

\* cited by examiner

ELECTRONIC DEVICE AND METHOD OF MANUFACTURING THE SAME

1. Technical Field

The present disclosure generally relates to an electronic device and a method of manufacturing the same.

2. Description of the Related Art

Monitoring biologically-relevant information helps determine a wide array of an individual's physiological characteristics. Integrating a monitoring device (such as a sensor) with a wearable device (such as a wearable patch) allows pertinent information to be collected in a continuous and nonintrusive manner, and thus has become increasingly popular.

SUMMARY

In one or more embodiments, the present disclosure provides an electronic device. The electronic device includes a first region, a second region, an electronic component, and a first sensing element. The second region is adjacent to the first region. The first region has a first pliability. The second region has a second pliability. The second pliability is greater than the first pliability. The electronic component is disposed at the first region. The first sensing element is disposed at the second region and electrically connected to the electronic component.

In one or more embodiments, the present disclosure provides an electronic device. The electronic device includes a carrier, an electronic component, and a first sensing element. The carrier has a first surface and a second surface opposite to the first surface. The electronic component is disposed on the first surface of the carrier. The first sensing element is disposed on the second surface of the carrier. The first sensing element is configured to displace relative to the electronic component by the carrier to sense a biosignal.

In one or more embodiments, the present disclosure provides a method of manufacturing an electronic device. The method includes: providing a pliable device including a carrier having a first surface and a second surface opposite to the first surface of the carrier; and disposing the sensing element relative to the electronic component to sense a biosignal. An electronic component is disposed on the first surface and a sensing element is disposed on the second surface.

BRIEF DESCRIPTION OF THE DRAWINGS

Aspects of the present disclosure are readily understood from the following detailed description when read with the accompanying figures. It should be noted that various features may not be drawn to scale. The dimensions of the various features may be arbitrarily increased or reduced for clarity of discussion.

Common reference numerals are used throughout the drawings and the detailed description to indicate the same or similar elements. The present disclosure will be more apparent from the following detailed description taken in conjunction with the accompanying drawings.

DETAILED DESCRIPTION

Figure 1:
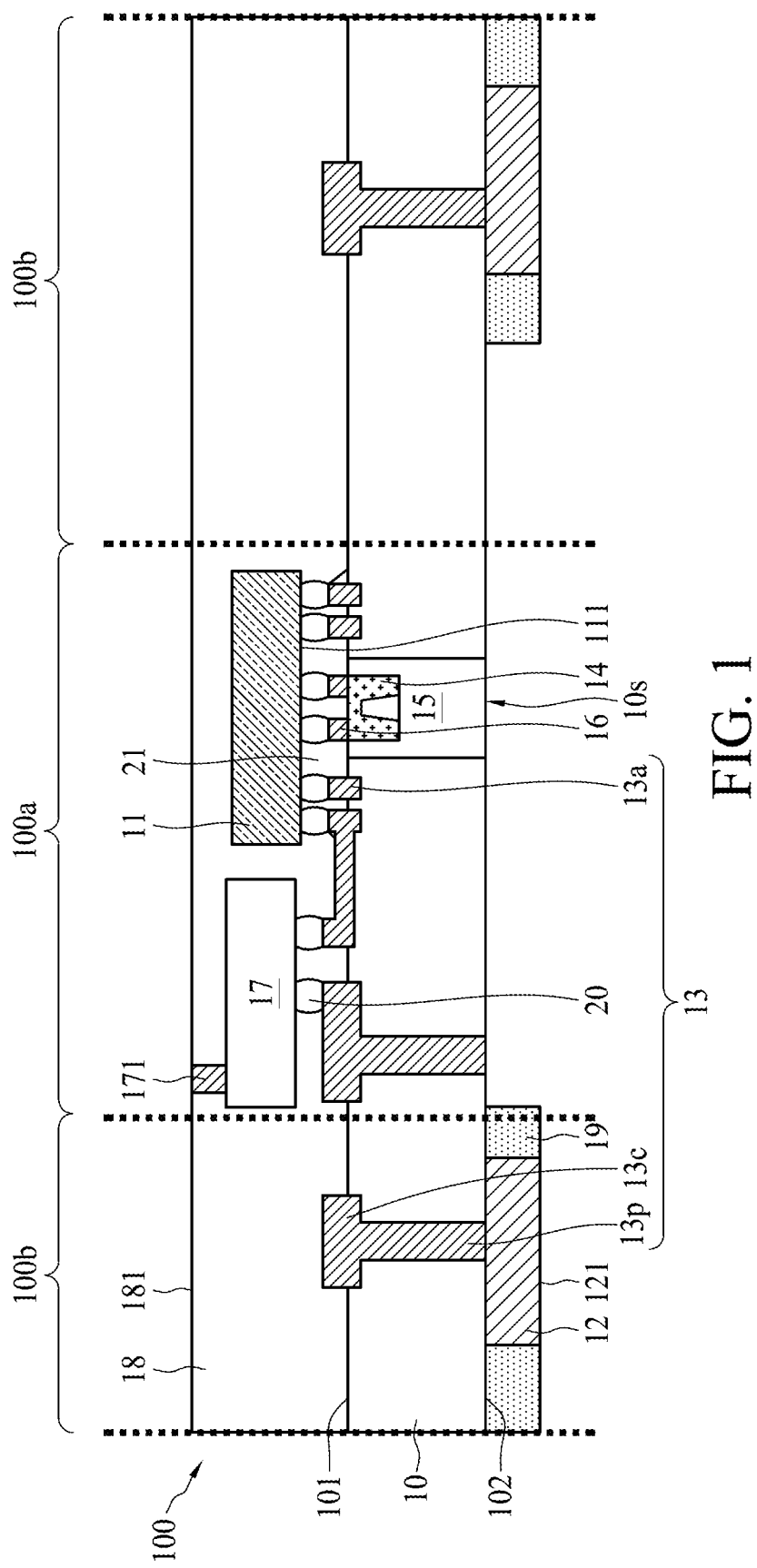
FIG. 1 illustrates a cross-sectional view of an electronic device in accordance with some embodiments of the present disclosure.

The following disclosure provides for many different embodiments, or examples, for implementing different features of the provided subject matter. Specific examples of components and arrangements are described below. These are, of course, merely examples and are not intended to be limiting. In the present disclosure, reference to the formation of a first feature over or on a second feature in the description that follows may include embodiments in which the first and second features are formed in direct contact, and may also include embodiments in which additional features may be formed between the first and second features, such that the first and second features may not be in direct contact. Besides, the present disclosure may repeat reference numerals and/or letters in the various examples. This repetition is for simplicity and clarity and does not in itself dictate a relationship between the various embodiments and/or configurations discussed.

Embodiments of the present disclosure are discussed in detail below. It should be appreciated, however, that the present disclosure provides many applicable concepts that can be embodied in a wide variety of specific contexts. The specific embodiments discussed are merely illustrative and do not limit the scope of the disclosure.

Figure 2:
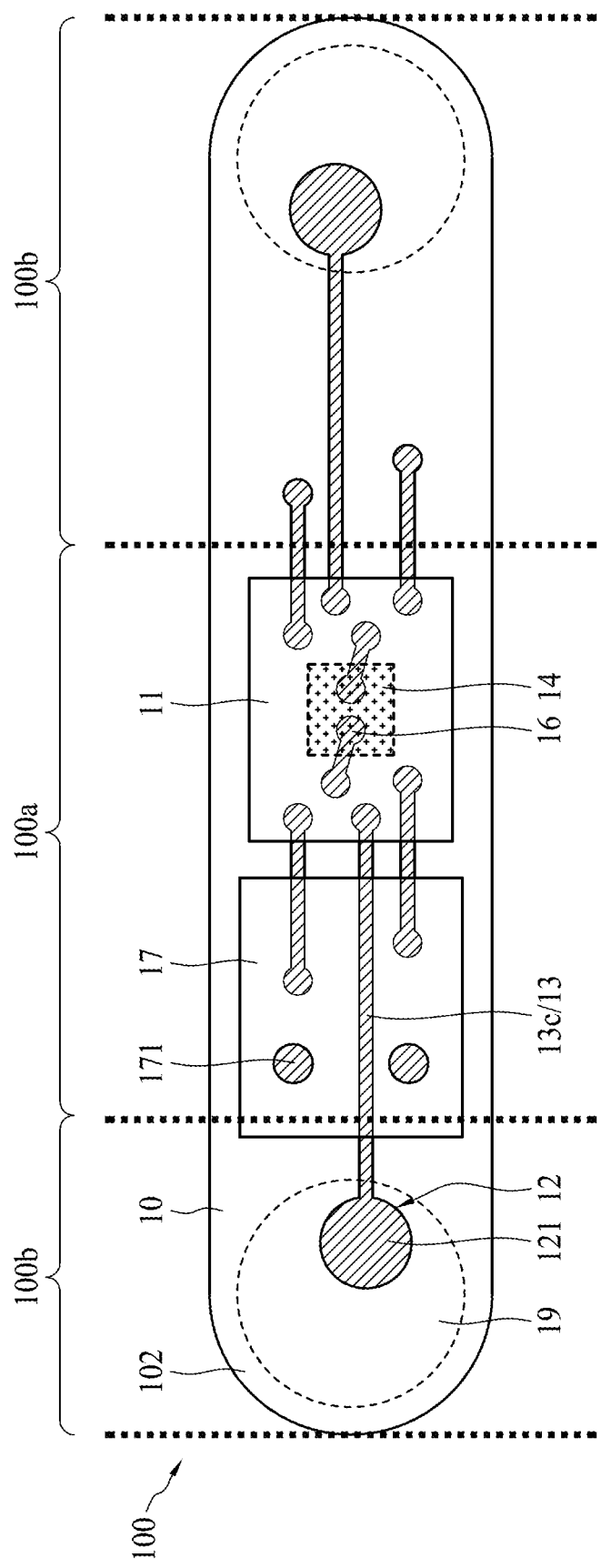
FIG. 2 illustrates a top view of an electronic device in accordance with some embodiments of the present disclosure.

FIG. 1 illustrates a cross-sectional view of an electronic device 100 in accordance with some embodiments of the present disclosure. FIG. 2 illustrates a top view of the electronic device 100 in accordance with some embodiments of the present disclosure. The electronic device 100 may be a wearable device, a portable device, a medical monitoring device, or any similar device(s). The electronic device 100 may include a substrate 10 (e.g., a carrier), an electronic component 11, a sensing element 12, a conductive structure 13, a sensing element 14, a protection layer 15, a conductive pad 16, a battery element 17, a protection layer 18, an adhesive layer 19, a connection element 20, and an underfill 21.

The substrate 10 may have a surface 101 and a surface 102 opposite thereto. The substrate 10 may be pliable. For example, the outline of the substrate 10 may be bendable, twistable, and/or stretchable. The substrate 10 may include a pliable material, a flexible material, or a soft material. The substrate 10 may include, but is not limited to, silicone or rubber. The substrate 10 may include a conductive layer coating on the surface 101 and/or the surface 102. The conductive layer of the substrate 10 may have a pattern. The conductive layer of the substrate 10 may be thin enough to be pliable.

The electronic component 11 may be disposed on the surface 101 of the substrate 10. The sensing element 12 may be disposed on or adjacent to the surface 102 of the substrate 10. Alternatively, the sensing element 12 may be integrated within the substrate 10. The electronic component 11 may be electrically connected to the sensing element 12 through the conductive structure 13. The sensing element 12 may be configured to detect a biosignal. The biosignal may include: a pulse travel time (PTT), an electroencephalogram (EEG), electrocardiogram (ECG), electromyogram (EMG), heart rate variability (HRV), oxygen saturation (unit: $SpO_2$), temperature, or other. The electronic component 11 may be configured to receive the biosignal from the sensing element 12. The electronic component 11 may be configured to process the biosignal to generate a processed data. In some embodiments, the electronic component 11 may be configured to amplify the biosignal. In some embodiments, the electronic component 11 may be configured to convert the biosignal or the amplified biosignal into digital data for the subsequent processing. The electronic component 11 may be configured to store the processed data. The electronic component 11 may be configured to transmit the processed data to an external device via attached wiring or wirelessly. The electronic component 11 may include a system-in-package (SiP). The electronic component 11 may include one or more dies.

In some embodiments, the sensing element 12 may be configured to receive or detect an electrical signal representing the received or detected biosignal. The sensing element 12 may be configured to transmit the electrical signal to the electronic component 11 through the conductive structure 13. The electronic component 11 may be configured to process, store, and/or transmit the electrical signal. In some embodiments, the sensing element 12 may be configured to detect a reference right-leg voltage. As shown in FIG. 1, the electronic device 100 may include a plurality of sensing elements, each of which may receive or detect different biosignals, different electrical signals, different thermal signals, or different optical signals.

The electronic component 11 may include a microcontroller, a sensor, a memory, or a wireless transmission module utilizing, for example, Bluetooth or Bluetooth Low Energy (BLE) protocols. The wireless transmission module may transmit the detected biosignal to an external processor. In an alternative embodiment, the electronic component 11 may process the detected biosignal. The electronic component 11 may determine, based on the processed biosignal, to send an alarm message to a device (e.g., an earphone, a mobile phone, or a watch) associated with the electronic device 100.

As shown in FIG. 1 and FIG. 2, the sensing element 12 may have a surface 121 exposed by the adhesive layer 19. The surface 121 of the sensing element 12 may be in contact with or close to subject's skin when the electronic device 100 is worn. The sensing element 12 may include a conductive pad. The conductive pad of the sensing element 12 may be non-overlapping with the electronic component 11 in a direction substantially perpendicular to the surface 101/surface 102 of the substrate 10. The sensing element 12 may include an electrode for electrical transmission or thermal transmission. As shown in FIG. 2, the shape of the sensing element 12 may be circular, elliptical, rectangular, triangular, or irregular.

The sensing element 12 may include a conductive material such as a metal, e.g., copper (Cu), gold (Au), silver (Ag), aluminum (Al), titanium (Ti), or the like. The conductive material of the sensing element 12 may include a conductive silicone, a thermal conductive silicone, a conductive rubber, a conductive sponge, a conductive fabric, or a conductive fiber.

The conductive structure 13 may be disposed in the substrate 10. The conductive structure 13 may include a conductive element 13a, a conductive element 13p, and a conductive element 13c. The conductive element 13a may include a conductive pad disposed on the surface 101 of the substrate 10. The conductive element 13p may include a conductive pillar extending through the substrate 10. The conductive element 13c may connect with the conductive element 13a and the conductive element 13p. The conductive structure 13 may be configured to electrically connect the elements of the electronic device 100, for example, the electronic component 11, the sensing element 12, and/or the battery element 17. The conductive structure 13 may include conductive material such as a metal or metal alloy. Examples include gold (Au), silver (Ag), aluminum (Al), copper (Cu), or an alloy thereof.

The sensing element 14 may be disposed below an active surface 111 of the electronic component 11. The sensing element 14 may be disposed between the active surface 111 of the electronic component 11 and the surface 101 of the substrate 10. The substrate 10 may define a cavity 10s penetrating the substrate 10. The cavity 10s may accommodate the sensing element 14. The sensing element 14 may be at least partially within the cavity 10s. The sensing element 14 may be configured to detect an optical signal. In some embodiments, the cavity 10s may be configured to guide a light beam from an external object to the sensing element 14 and vice versa. The protection layer 15 may be disposed within the cavity 10s. The protection layer 15 may cover the sensing element 14. The protection layer 15 may be transparent. The protection layer 15 may include, but is not limited to, a molding compound without fillers. In other embodiments, the sensing element 14 may be or include a non-optical sensing device (e.g., a motion sensor, a temperature sensor, or the like), and in such case, the cavity 10s and the protection layer 15 may be omitted.

The electronic component 11 may be electrically connected to the sensing element 14 through the conductive pad 16. The sensing element 14 may be configured to detect a biosignal. The biosignal may include a PTT, an EEG, ECG, EMG, HRV, oxygen saturation (unit: $SpO_2$), temperature, or others. The electronic component 11 may be configured to receive the biosignal from the sensing element 14. The conductive pad 16 may include a conductive material such as a metal or metal alloy. Examples include gold (Au), silver (Ag), aluminum (Al), copper (Cu), or an alloy thereof.

In an alternative embodiment, the sensing element 14 may be integrated within the electronic component 11. The integrated sensing element 14 may be substantially aligned with the cavity 10s or protection layer 15, such that the integrated sensing element 14 can receive an optical signal through the protection layer 15. In other words, no sensing element is disposed within the cavity 10s. In an alternative embodiment, the sensing element 14 may be integrated within the electronic component 11 and the sensing element 14 may be or include a non-optical sensing device (e.g., a motion sensor, a temperature sensor, or the like), and in such case, the cavity 10s and the protection layer 15 may be omitted.

The battery element 17 may be disposed on the surface 101 of the substrate 10. The battery element 17 may be configured to supply power to the electronic component 11 and/or the sensing element 14. The battery element 17 may be electrically connected to the electronic component 11. The battery element 17 may include an electrode 171 exposed from the protection layer 18. The electrode 171 of the battery element 17 may be configured to connect an external charger. The battery element 17 may be configured to be charged through connected wiring. The battery element 17 may include a Li-ion battery. In some embodiments, the electronic device 100 may include a plurality of battery elements 17.

The protection layer 18 may be disposed on the surface 101 of the substrate 10. The protection layer 18 may be pliable. For example, the outline of the protection layer 18 may be bendable, twistable, and/or stretchable. The protection layer 18 may cover the electronic component 11. The protection layer 18 may cover the battery element 17. The protection layer 18 may include a molding compound without fillers.

The adhesive layer 19 is disposed on the surface 102 of the substrate 10. The adhesive layer 19 may surround the conductive pad of the sensing element 12. The adhesive layer 19 may cover the conductive pad of the sensing element 12. The adhesive layer 19 may be in contact with subject's skin (e.g., user's skin or user's body part) when the electronic device 100 is worn. The adhesive layer 19 may adhere to subject's skin when the electronic device 100 is worn. The adhesive layer 19 may include, but is not limited to, glue, tape, patch, die attach film (DAF), or others.

As shown in FIG. 1 and FIG. 2, the electronic device 100 may include a region 100a and a region 100b adjacent thereto. The electronic component 11 may be disposed at the region 100a. The battery element 17 may be disposed at the region 100a. The electronic component 11 and the battery element 17 may be relatively rigid. As such, the region 100a may have relatively low pliability. The area of the region 100a may be determined by the location of at least the electronic component 11 and/or the battery element 17. The conductive structure 13 and the sensing element 12 (e.g., a conductive pad) may be disposed at the region 100b. The adhesive layer 19 may be disposed at the region 100b. In other words, no rigid element is disposed at the region 100b. The region 100b may have relatively high pliability. The pliability of the region 100b may be greater than that of the region 100a. Furthermore, the curvature of the region 100a may be lower than the curvature of the region 100b when the electronic device 100 is worn. As shown in FIG. 1, the electronic device 100 may include an extra region (e.g., the region 100b on the left side) adjacent to the region 100a. An extra sensing element may be disposed at the extra region and configured to detect a biosignal different from the biosignal detected by the sensing element 12. The total area of the region 100b and the extra region may be greater than the area of the region 100a. The region 100b and the extra region may be separated by the region 100a.

As previously discussed, the electronic component 11 may have multiple functions (processing, transmission, and/or storage of biosignals) and still be relatively small owing to its manufacture using advanced packaging, e.g., SiP. The sensing elements 12 and 14, the electronic component 11, and the battery element 17 may be integrated into the substrate 10 by manufacture with advanced packaging.

Hence, the size of the electronic device 100 may be significantly reduced. When the electronic device 100 is worn, the region 100b with relatively high pliability may conform to the topography of subject's skin or any body part(s), such as a finger, wrist, elbow, arm, chest, neck, ear, thigh, knee, leg, foot, or others. The electronic device 100 is compact, small, soft, and pliable enough to be worn for an extended time period without discomfort. Furthermore, the area of the region 100b may be greater than the area of the region 100a to provide improved adhesion between the electronic device 100 and a subject or an object.

The connection element 20 may be disposed between the conductive structure 13 and the battery element 17. The battery element 17 may be electrically connected to the conductive structure 13 through the connection element 20. The connection element 20 may be disposed between the conductive structure 13 and the electronic component 11. The electronic component 11 may be electrically connected to the conductive structure 13 through the connection element 20. The connection element 20 may be disposed between the electronic component 11 and the sensing element 14. The electronic component 11 may be electrically connected to the sensing element 14 through the connection element 20 and the conductive pad 13. The connection element 20 may include, for example, a solder ball or a controlled collapse chip connection (C4) bump.

The underfill 21 may be disposed between the active surface of the electronic component and the surface 101 of the substrate 10. The underfill 21 may enclose the conductive element 13a, the conductive pad 16, and the connection element 20. In an alternative embodiment, the electronic device 100 may exclude an underfill.

Figure 3:
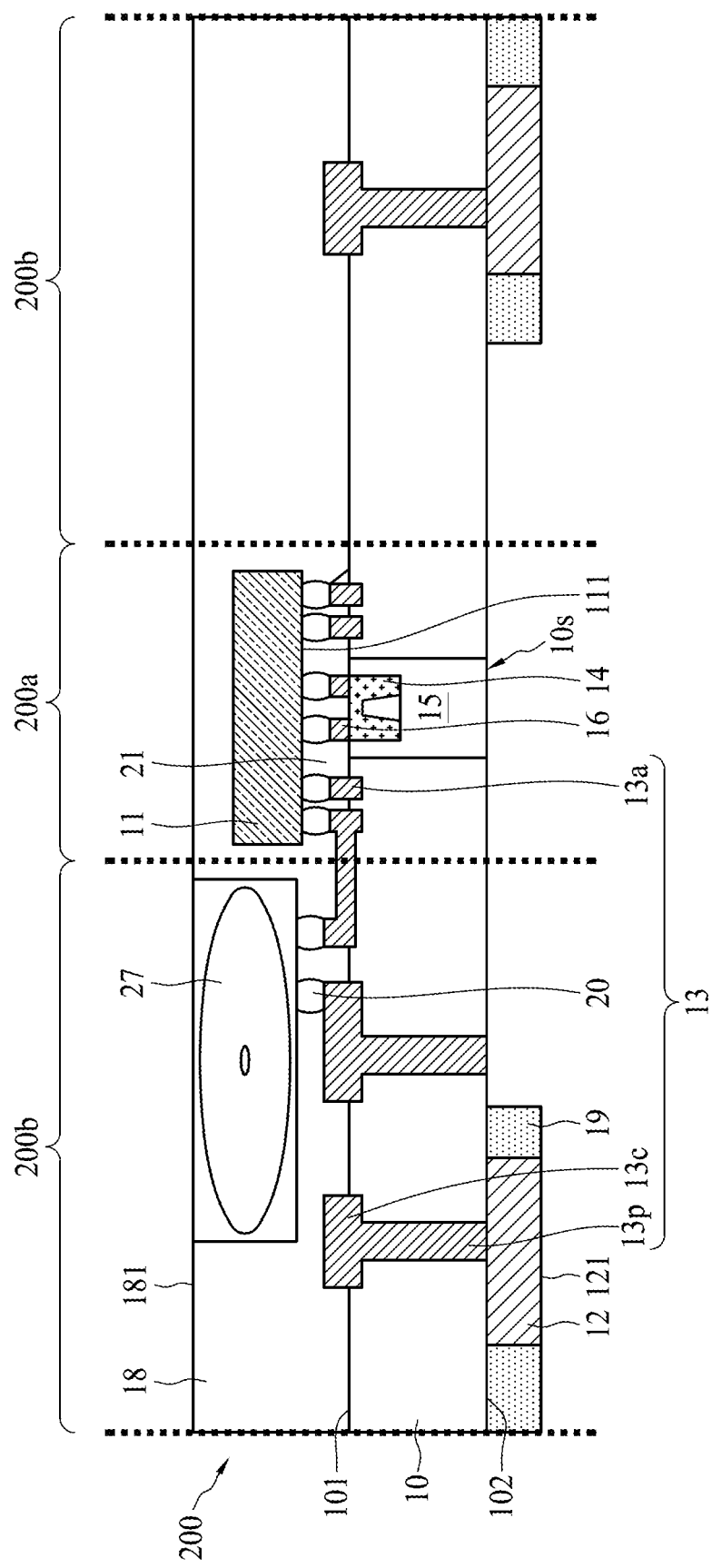
FIG. 3 illustrates a cross-sectional view of an electronic device in accordance with some embodiments of the present disclosure.

FIG. 3 illustrates a cross-sectional view of an electronic device 200 in accordance with some embodiments of the present disclosure. The semiconductor electronic device 200 of FIG. 3 is similar to the electronic device 100 of FIG. 1 and FIG. 2 with differences therebetween as follow.

The electronic device 200 may include a battery element 27, rather than the battery element 17 as illustrated in FIG. 1. The battery element 27 may be disposed on the surface 101 of the substrate 10. The battery element 27 may overlap with the sensing element 12 in a direction substantially perpendicular to the surface 101/surface 102 of the substrate 10. The battery element 27 may be pliable. The battery element 27 may include coils for storing electricity. The battery element 27 may be configured to be charged wirelessly The electronic device 200 may include a region 200a and the 200b adjacent the region 200a. The battery element 27 may be disposed at the region 200b. The pliability of the region 200b may be greater than the pliability of the region 200a. The curvature of the region 200a may be lower than the curvature of the region 200b when the electronic device 200 is worn by a subject. The ratio of the region 200b and the region 200a is greater than that of the region 100b and the region 100a of the electronic device 100. As such, the electronic device 200 may be more conformal to subject's skin or other body parts than the electronic device 100.

Figure 4:
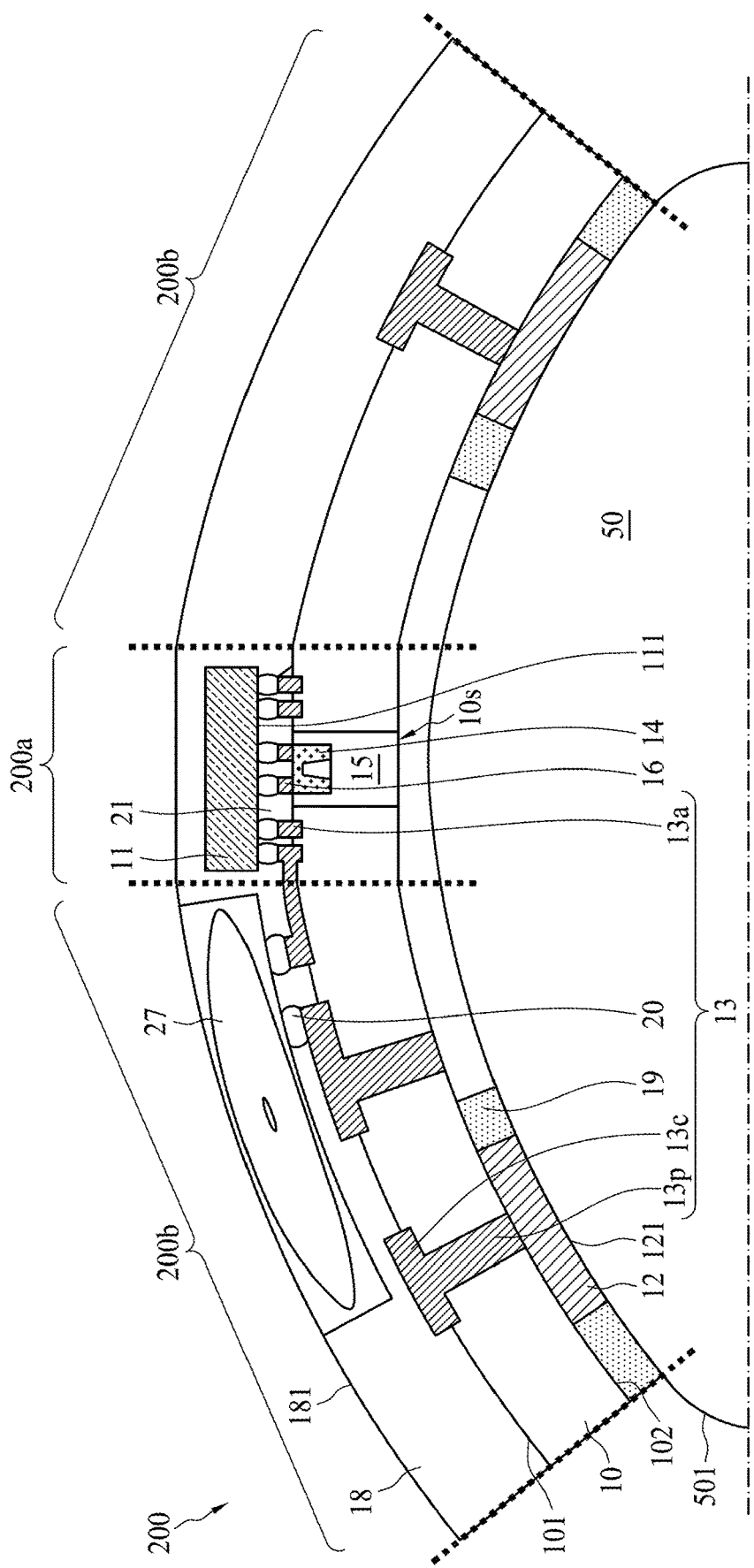
FIG. 4 is a schematic diagram of an electronic device being attached to an object in accordance with some embodiments of the present disclosure.

FIG. 4 is a schematic diagram of the electronic device 200 attached to an object 50 in accordance with some embodiments of the present disclosure. The object 50 may have a curved surface 501 facing the electronic device 200. As shown in FIG. 4, the sensing element 12 may be bent to conform to the curved surface 501. The surface 121 of the sensing element 12 may be conform to the curved surface 501. The adhesive layer 19 may be conform to the curved surface 501. Furthermore, the region 200b may be bent to conform to the curved surface 501, while the region 200a may be rigid enough to retain the shape. The curvature of the region 200a may be lower than the curvature of the region 200b when the electronic device 100 is worn. The battery element 27 may be bent, while the electronic component 11 may be rigid enough to retain the shape. The object 50 may be a body part(s), such as a finger, wrist, elbow, arm, chest, neck, ear, thigh, knee, leg, foot, or other. The curved surface may be the skin of the body part as discussed.

As shown in FIG. 4, the sensing element 12 may be configured to physically connect to a user's body part. The electronic component 11 may be physically separated from the user's body part.

Figure 5:
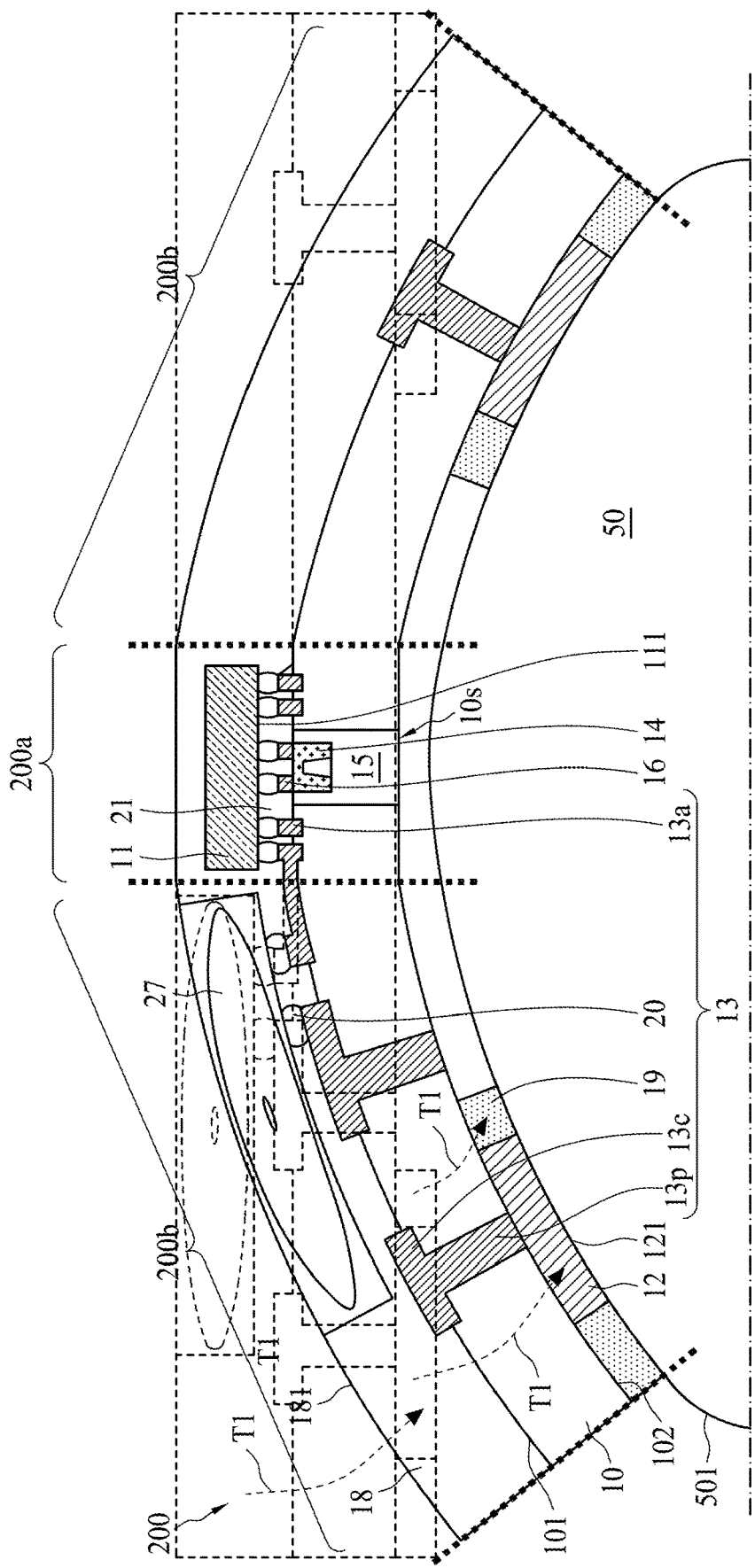
FIG. 5 illustrates a displacement of an electronic device when being attached to an object in accordance with some embodiments of the present disclosure.

FIG. 5 illustrates a displacement of the electronic device 200 when being attached to the object 50 in accordance with some embodiments of the present disclosure. The dotted line shows original shape and position of the electronic device 200 before being attached to the object 50. As shown in FIG. 5, when the electronic device 200 is attached to the object 50, the sensing element 12 may be configured to displace relative to the electronic component 11 by the substrate 10. The sensing element 12 may be configured to displace in a trajectory T1 relative to the electronic component 11. Such a displacement can make the surface 121 of the sensing element 12 conform to the curved surface 501 of the object 50. The sensing element 12 may be configured to sense a biosignal with no obstacle. The protection layer 18 may include a portion overlapping with the sensing element 12 in a direction perpendicular to the surface 101 of the substrate 10. The portion of the protection layer 18 may be configured to displace relative to the electronic component 10. The portion of the protection layer 18 may be configured to displace in the trajectory T1 relative to the electronic component 11. The adhesive layer 19 and the sensing element 12 may be configured to displace in the same trajectory (e.g., the trajectory T1) relative to the electronic component 10.

Figure 6:
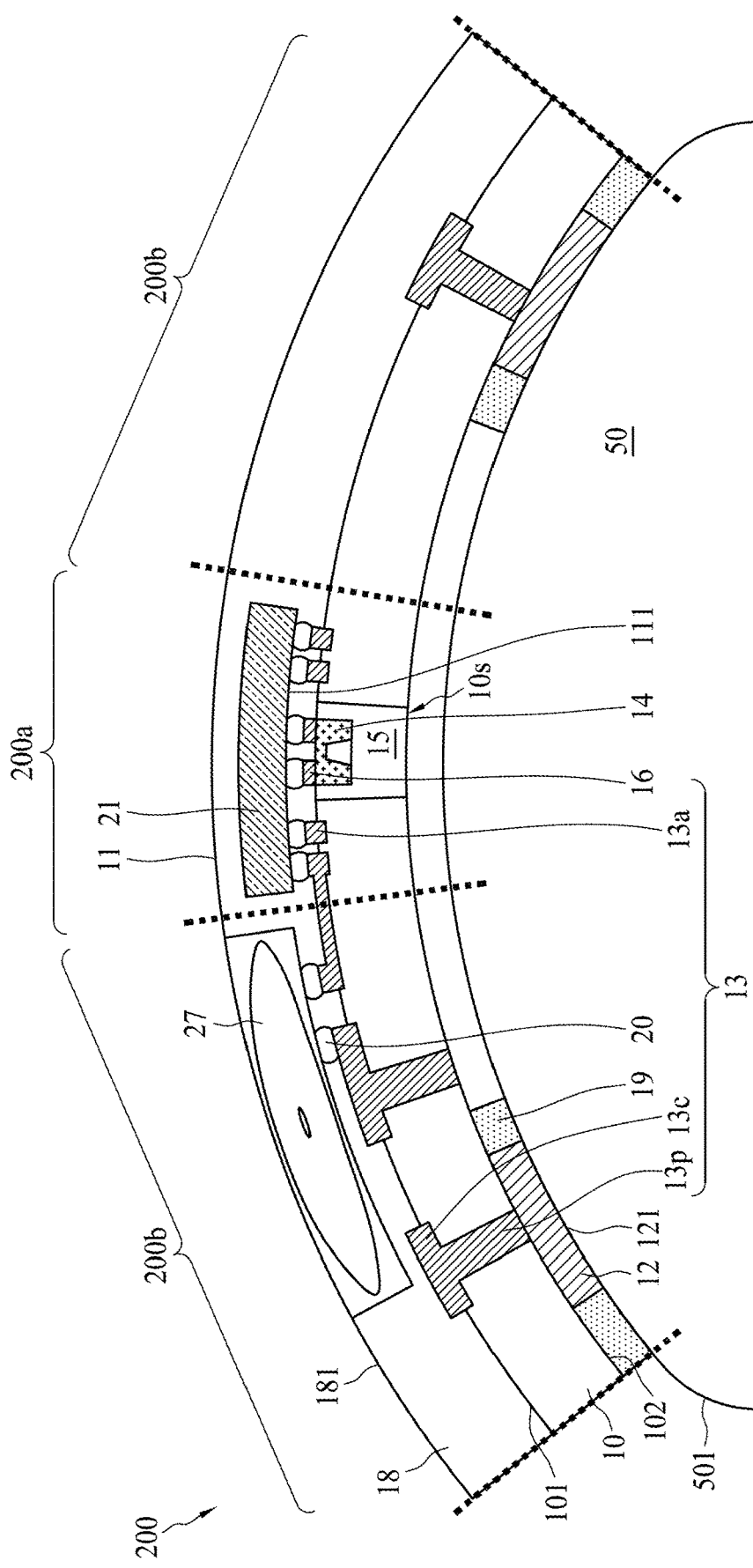
FIG. 6 is a schematic diagram of an electronic device attached to an object in accordance with some embodiments of the present disclosure.

FIG. 6 illustrates a schematic diagram of the electronic device 200 attached to the object 50 in accordance with some embodiments of the present disclosure. The sensing element 12 may be bent to conform to the curved surface 501. The surface 121 of the sensing element 12 may be conform to the curved surface 501. The adhesive layer 19 may be conform to the curved surface 501. Furthermore, the region 200b may be bent to conform to the curved surface 501, and the region 200a may be bent to conform to curved surface 501. The battery element 27 may be bent, while the electronic component 11 may be bent to conform to the curved surface 501.

Figure 7:
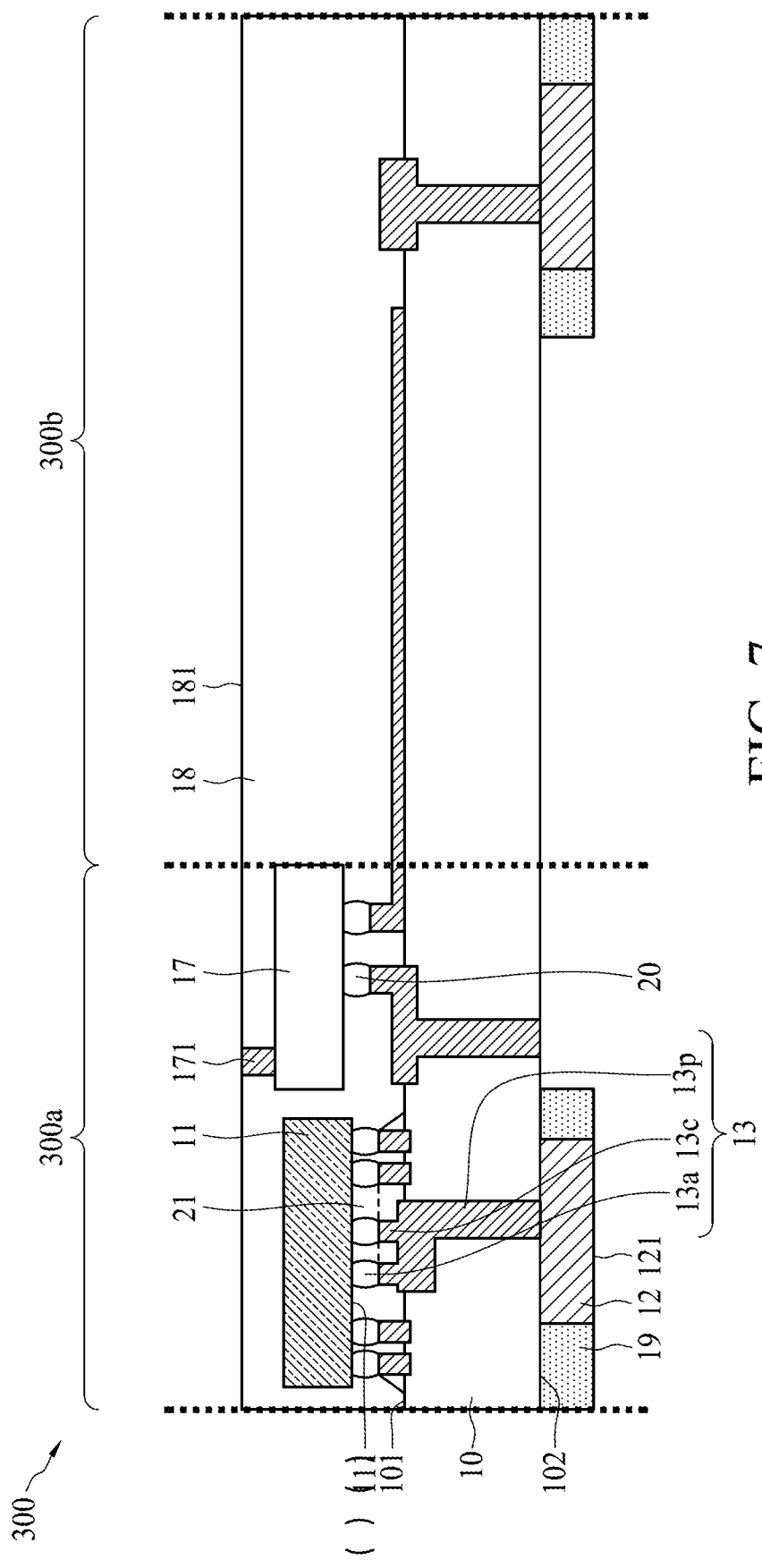
FIG. 7 illustrates a cross-sectional view of an electronic device in accordance with some embodiments of the present disclosure.

FIG. 7 illustrates a cross-sectional view of an electronic device 300 in accordance with some embodiments of the present disclosure. The semiconductor electronic device 300 of FIG. 7 is similar to the electronic device 100 of FIG. 1 and FIG. 2; with differences therebetween as follow.

The conductive pad of the sensing element 12 may overlap with the electronic component 11 in a direction substantially perpendicular to the surface 101/surface 102 of the substrate 10. The electronic component 11 may exclude the sensing element 14. In an alternative embodiment, the sensing element 14 may be integrated within the electronic component 11.

The electronic device 300 may include a region 300a and a region 300b. The electronic component 11, the battery element 17, and the sensing element 12 may be disposed at the region 300a. The pliability of the region 300b may be greater than the pliability of the region 300a. The curvature of the region 300a may be lower than the curvature of the region 300b when the electronic device 300 is worn.

Figure 8:
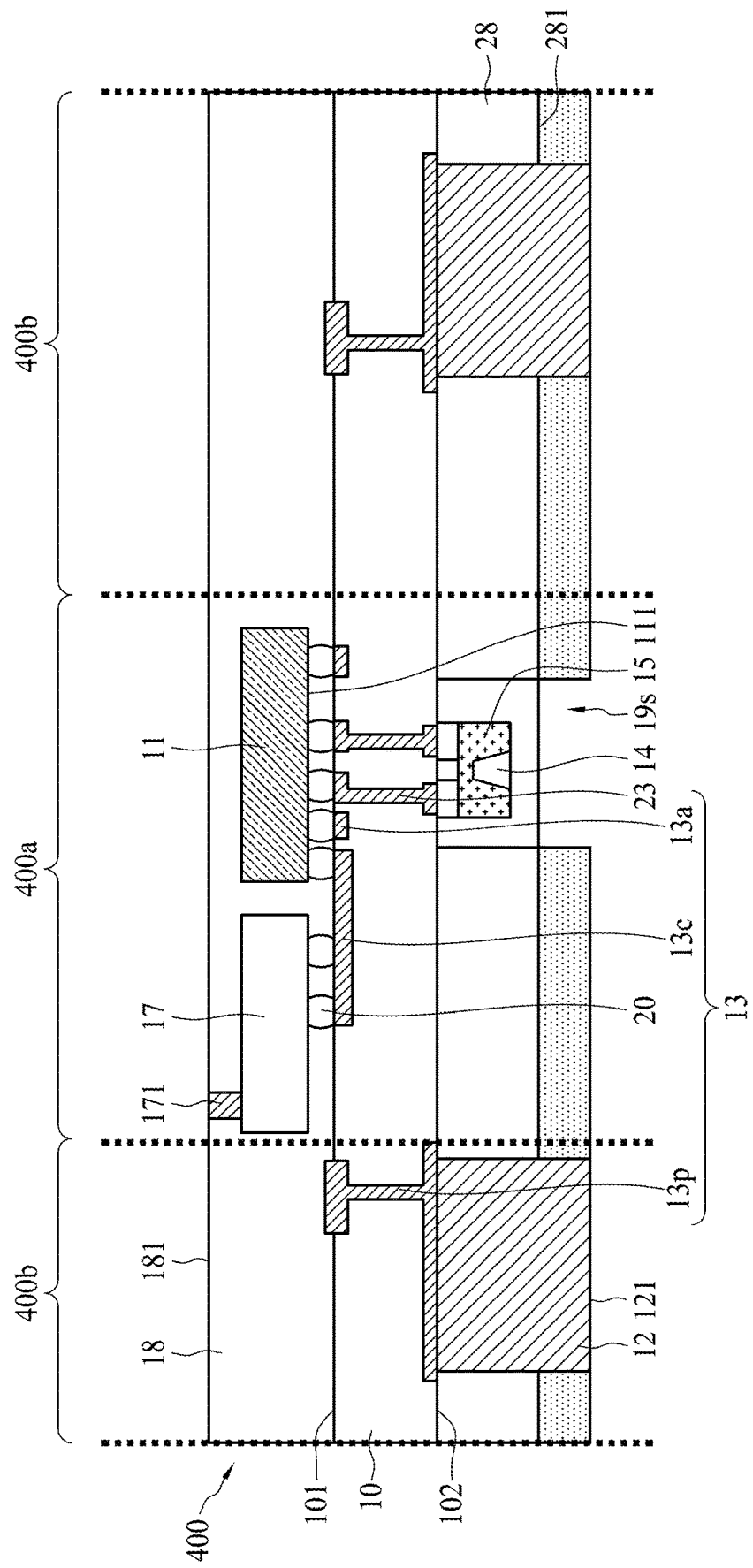
FIG. 8 illustrates a cross-sectional view of an electronic device in accordance with some embodiments of the present disclosure.

FIG. 8 illustrates a cross-sectional view of an electronic device in accordance with some embodiments of the present disclosure. The semiconductor electronic device 400 of FIG. 8 is similar to the electronic device 100 of FIG. 1 and FIG. 2; with differences therebetween as follow.

The electronic device may include a protection layer 28 disposed on the surface 102 of the substrate 10. The protection layer 28 may be pliable. For example, the outline of the protection layer 28 may be bendable, twistable, and/or stretchable. The sensing element 14 may be disposed on the surface 102 of the substrate 10 and surrounded by the protection layer 28. The protection layer 28 may include material similar to the protection layer 18. Owing to the extra protection layer 28, the sensing element 12 may be extend further perpendicular to the surface 101/surface 102 of the substrate 10.

The protection layer 28 may have a surface 281 facing away from the substrate 10. The adhesive layer 19 may be disposed on the surface 281 of the protection layer 28. The adhesive layer 19 may define an opening 19s. The opening 19s may be substantially aligned with the sensing element 14 and/or the protection layer 15. The opening 19s allows the sensing element 14 to receive or detect an optical signal.

The electronic device 400 may include a conductive element 23 configured to electrically connect the electronic component 11 with the sensing element 14. The conductive element 23 may be disposed on the surface 102 of the substrate 10 and exposed from the protection layer 28. The conductive element 23 may include a conductive pillar extending through the substrate 10. The conductive element 23 may include a conductive material such as a metal or metal alloy. Examples include gold (Au), silver (Ag), aluminum (Al), copper (Cu), or an alloy thereof.

Similar to the electronic device 200 as illustrated in FIG. 5, the electronic device 400 may have a displacement when being attached to an object (e.g., the object 50). The protection layer 28 may include a portion overlapping with the sensing element 12 in a direction perpendicular to the surface 101 of the substrate 10. The portion of the protection layer 28 may be configured to displace in the trajectory T1 relative to the electronic component 11. A portion of the adhesive layer 19 on the protection layer 28 may be configured to displace in the trajectory T1 relative to the electronic component 10.

FIG. 9, FIG. 10, FIG. 11, FIG. 12, FIG. 13, FIG. 14, and FIG. 15 each illustrate one or more stages of an exemplary method for manufacturing a semiconductor device package according to some embodiments of the present disclosure.

Figure 9:
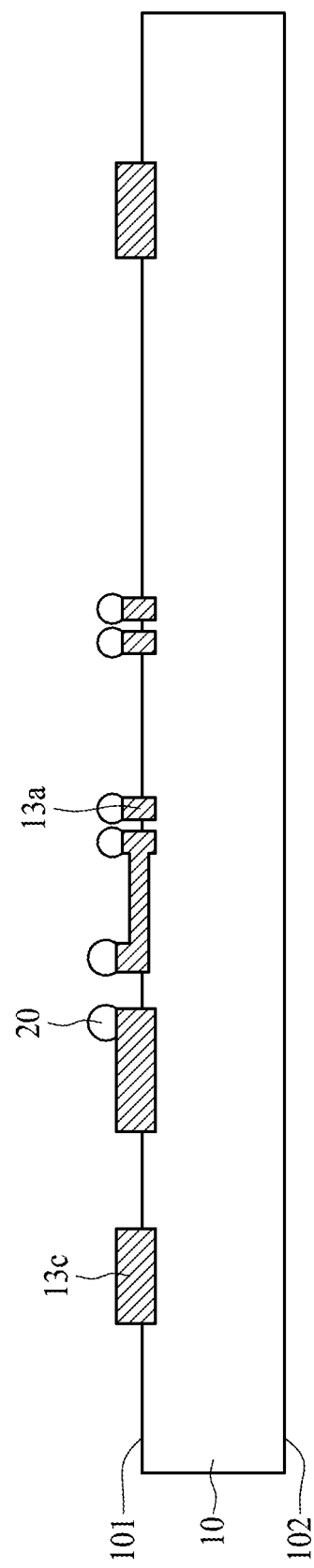
FIG. 9, FIG. 10, FIG. 11, FIG. 12, FIG. 13, FIG. 14, and FIG. 15 each illustrate one or more stages of an exemplary method for manufacturing a semiconductor device package according to some embodiments of the present disclosure.
Figure 10:
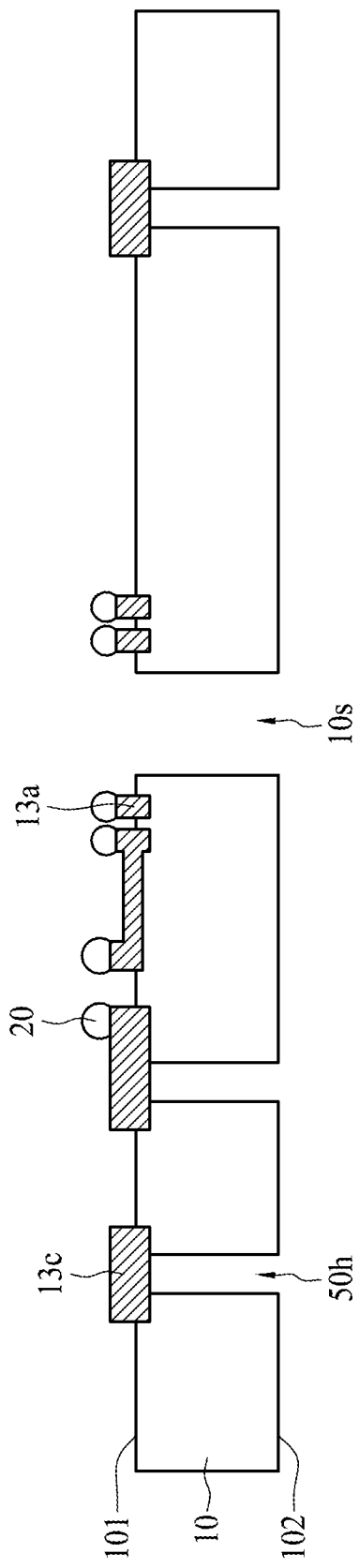

Referring to FIG. 9, a substrate 10 may be provided. The substrate may have a surface 101 and a surface 102 opposite thereto. A conductive element 13a may be disposed on the surface 101 of the substrate 10. A conductive element 13c may be disposed on the surface 101 of the substrate 10. A connection element 20 may be disposed on the conductive element 13a or the conductive element 13c. Referring to FIG. 10, the substrate 10 may be etched to form a cavity 10s by, for example but not limited to, laser drilling. The cavity 10s may be a through-via. The substrate 10 may be etched to form a hole 50h by, for example but not limited to, laser drilling. The etch process to form the hole 50h may use the conductive element 13c as an etch-stop layer.

Figure 11:
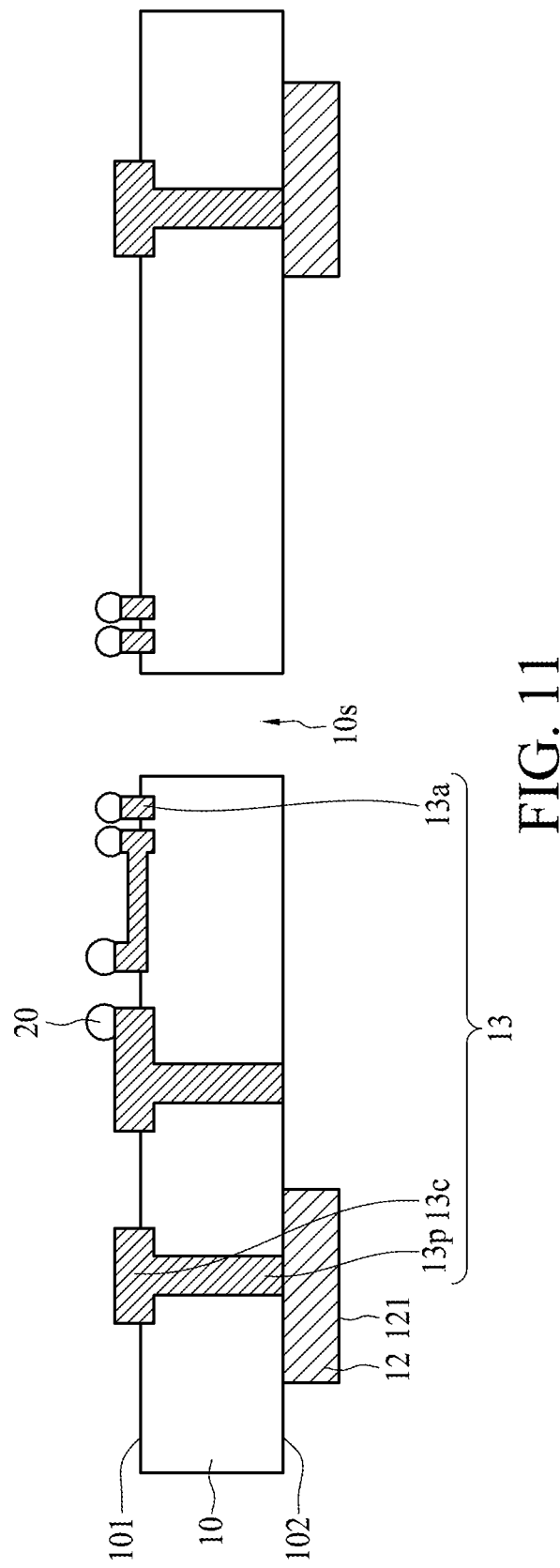

Referring to FIG. 11, a conductive element 13p may be formed in the hole 50h by, for example but not limited to, sputtering, or electroplating. The conductive elements 13a, 13c, and 13p are referred to as a conductive structure 13 in the following. Furthermore, a sensing element 12 may be formed on the surface 102 of the substrate 10 by, for example but not limited to, sputtering or electroplating. The sensing element 12 may have a surface 121 facing away from the substrate 10. The sensing element 12 may be in contact with the conductive structure 13.

Figure 12:
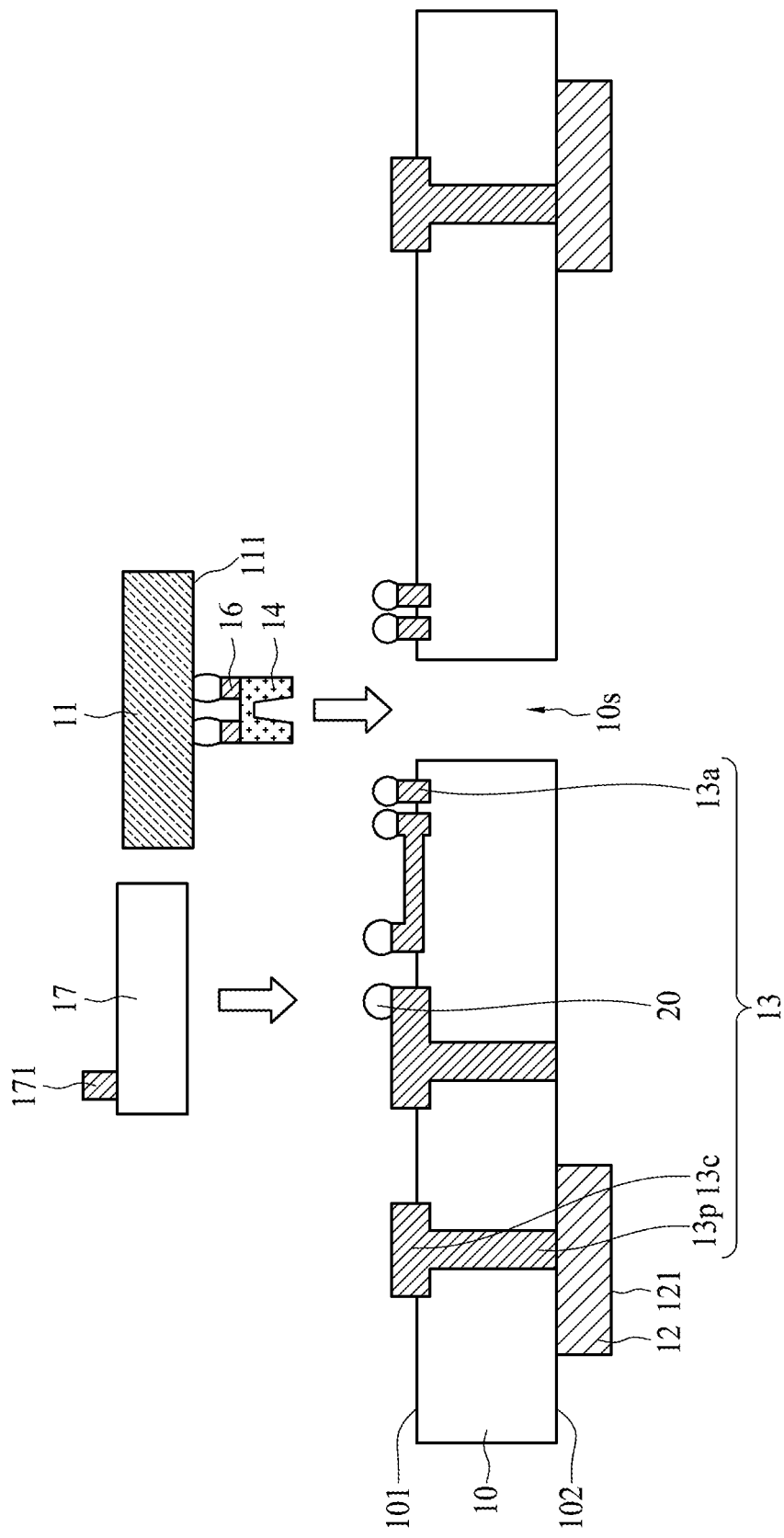
Figure 13:
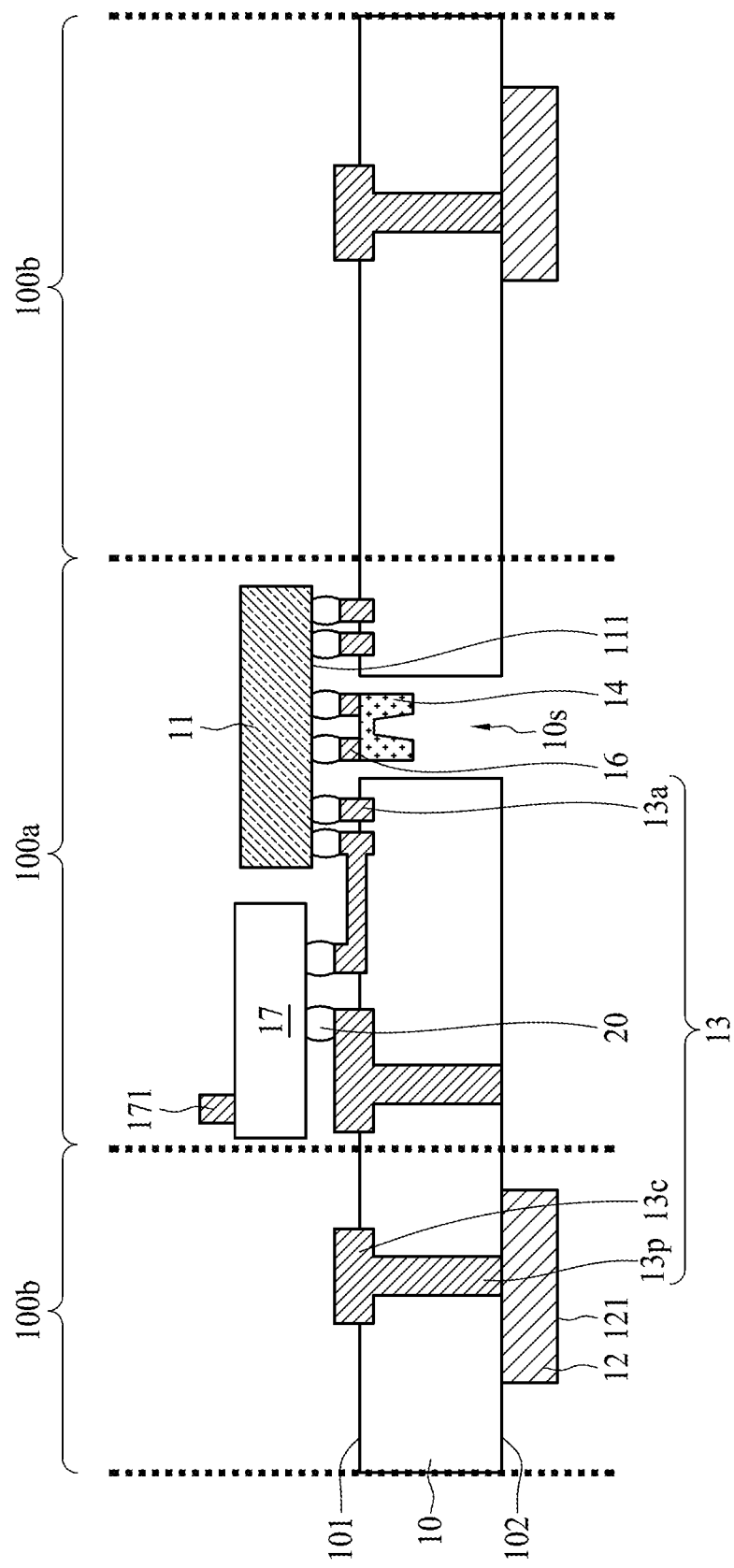

Referring to FIG. 12, an electronic component 11, a sensing element 14, and a battery element 17 may be provided. The sensing element 14 may be attached to an active surface 111 of the electronic component 11 through a conductive pad 16 and a connection element. The electronic component 11 along with the sensing element 14 may be attached to the substrate 10 through the connection element 20. The sensing element 14 and/or the electronic component 11 may be substantially aligned with the cavity 10s. The battery element 17 may include an electrode 171 and may be attached to the substrate 10 through the connection element 20. In some embodiments, a pliable device including a substrate 10 (e.g., a carrier) may be provided. The substrate 10 may have a surface 101 and a surface 102 opposite thereto. An electronic component (e.g., the electronic component 11) may be disposed on the surface 101 and a sensing element (e.g., the sensing element 12) may be disposed on the surface 102. The sensing element 12 may be configured to displace relative to the electronic component 11 to sense a biosignal Referring to FIG. 13, the sensing element 14 may be placed at least partially within the cavity 10s. According to the location of the electronic component 11 and the battery element 17, a region 100a and a region 100b can be defined. Since rigid elements, e.g., the electronic component 11 and the battery element 17, are located at the region 100a, the pliability of the region 100b may be greater than that the region 100a.

Figure 14:
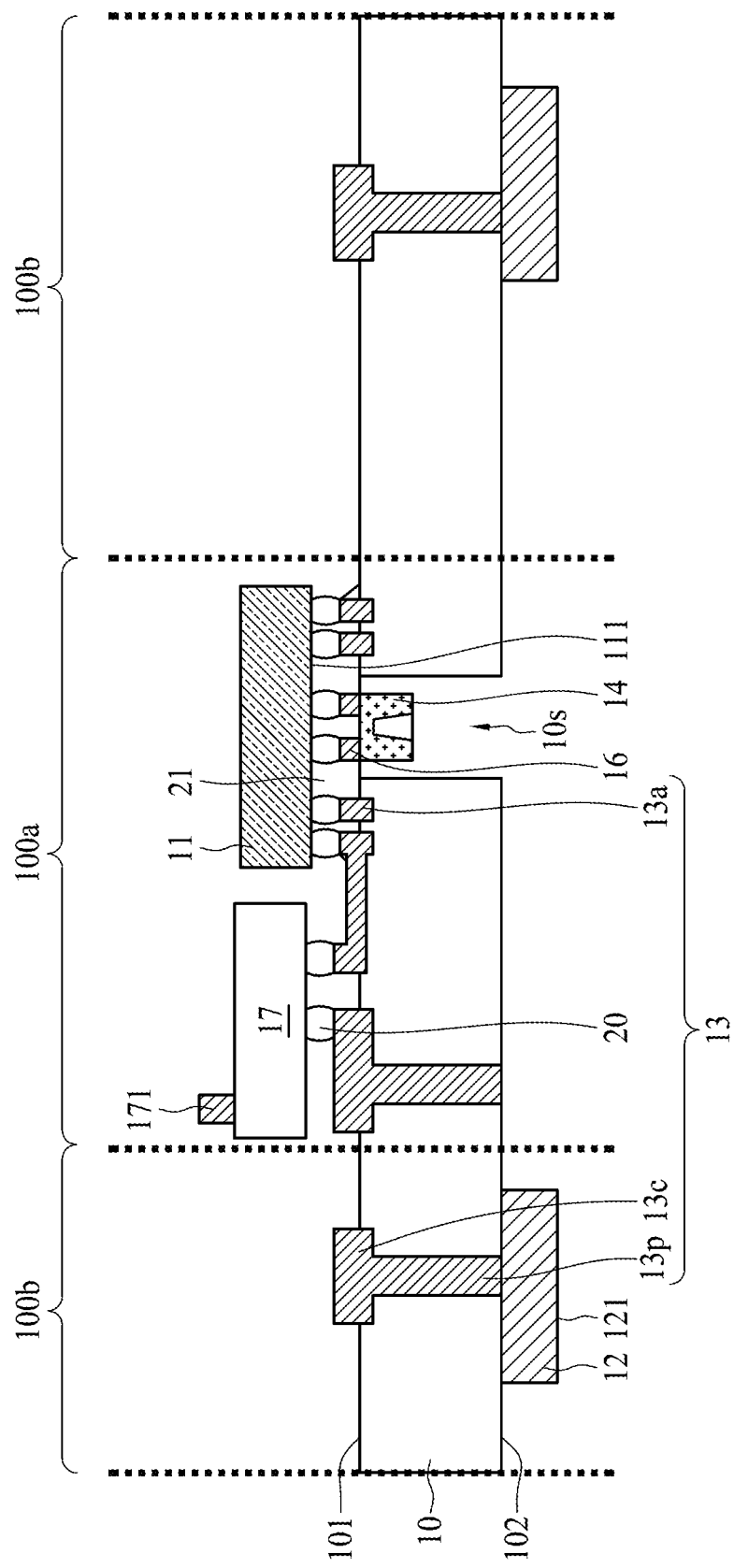

Referring to FIG. 14, an underfill may be formed between the active surface 111 of the electronic component 11 and the surface 101 of the substrate 10.

Figure 15:
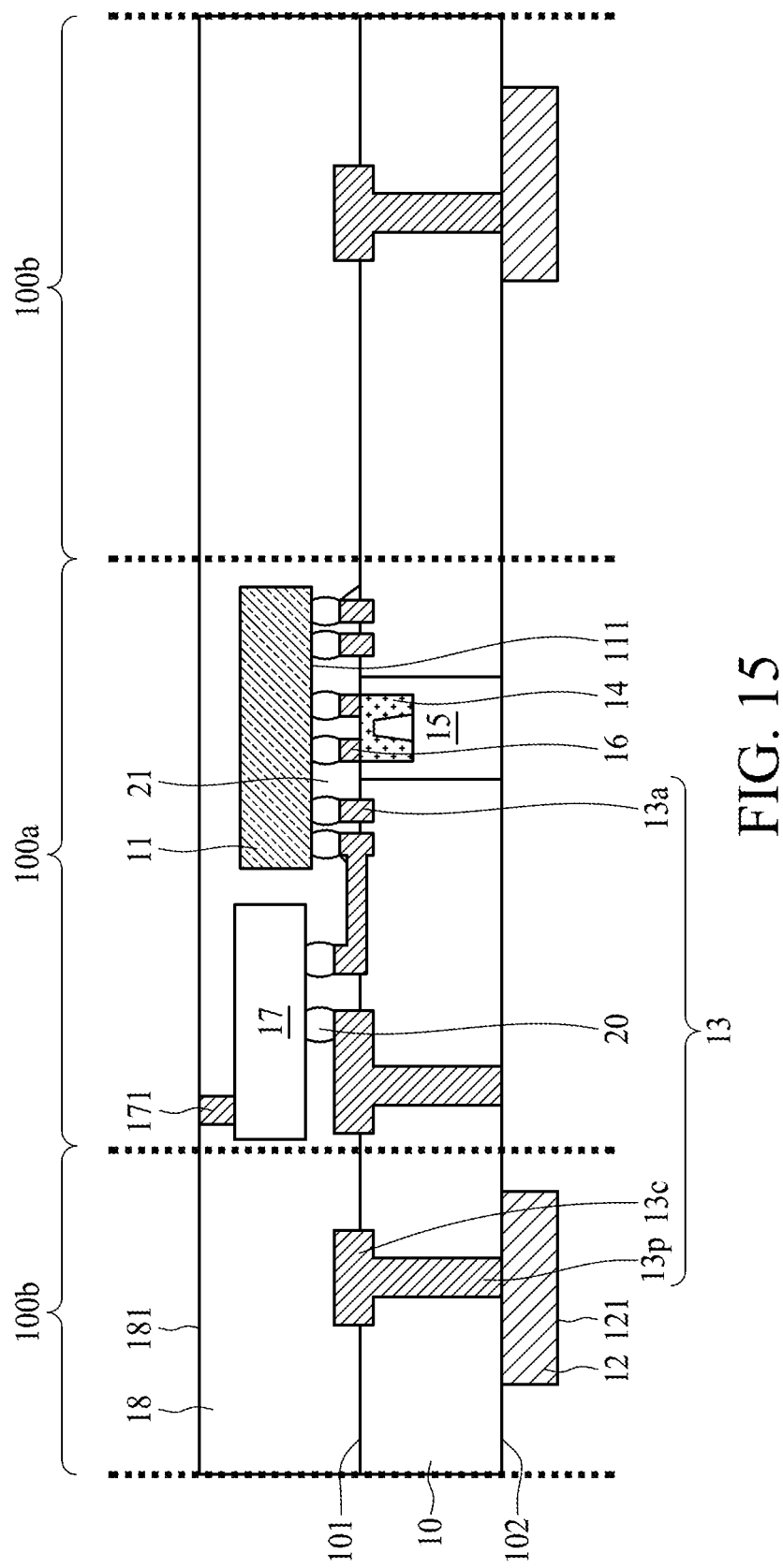

Referring to FIG. 15, a protection layer 18 may be formed on the surface 101 of the substrate 10. The protection layer 18 may surround the electronic component 11 and/or the battery element 17. The protection layer 18 may cover the electronic component 11 and/or the battery element 17. The protection layer 18 may have a surface 181 facing away from the substrate 10. The electrode 171 of the battery element 17 may be exposed by the surface 181 of the protection layer 18.

Still referring to FIG. 15, a protection layer 15 may be formed in the cavity 10s. In some embodiments, the protection layer 15 may fill in the cavity 10s.

Afterwards, an adhesive layer 19 may be formed on the surface 102 of the substrate 10 to form the electronic device 100 as illustrated in FIG. 1 and FIG. 2. The adhesive layer 19 may surround the sensing element 12. In some embodiments, the adhesive layer 19 may cover the sensing element 12.

In an alternative embodiment, the sensing element 14 may be attached to the electronic component 11 after the electronic component 11 has been attached to the substrate 10. The sensing element 14 may be configured to detect various signals. The sensing element 14 may be multi-functional. As such, the protection layer 15 can be omitted. Furthermore, the protection layer 18 may include a void and may be unable to completely encapsulate the electronic component 11, which may affect the reliability of the electronic device 100. The electronic component 11 may be replaced with a new electronic component, while the sensing element 14 can remain in the electronic device 100.

Spatially relative terms, such as "beneath," "below," "lower," "above," "upper," "left," "right" and the like, may be used herein for ease of description to describe one element or feature's relationship to another element(s) or feature(s) as illustrated in the figures. The spatially relative terms are intended to encompass different orientations of the device in use or operation, in addition to the orientation depicted in the figures. The apparatus may be otherwise oriented (rotated 90 degrees or at other orientations) and the spatially relative descriptors used herein may likewise be interpreted accordingly. It should be understood that when an element is referred to as being "connected to" or "coupled to" another element, it may be directly connected to or coupled to the other element, or intervening elements may be present.

As used herein, the terms "approximately", "substantially", "substantial" and "about" are used to describe and account for small variations. When used in conduction with an event or circumstance, the terms can refer to instances in which the event or circumstance occurs precisely as well as instances in which the event or circumstance occurs to a close approximation. As used herein with respect to a given value or range, the term "about" generally means within ±10%, ±5%, ±1%, or ±0.5% of the given value or range. Ranges can be expressed herein as from one endpoint to another endpoint or between two endpoints. All ranges disclosed herein are inclusive of the endpoints unless specified otherwise. The term "substantially coplanar" can refer to two surfaces within micrometers (μm) of lying along the same plane, such as within 10 within 5 within 1 μm, or within 0.5 μm of lying along the same plane. When referring to numerical values or characteristics as "substantially" the same, the term can refer to the values lying within ±10%, ±5%, ±1%, or ±0.5% of an average of the values.

The foregoing outlines features of several embodiments and detailed aspects of the present disclosure. The embodiments described in the present disclosure may be readily used as a basis for designing or modifying other processes and structures for carrying out the same or similar purposes and/or achieving the same or similar advantages of the embodiments introduced herein. Such equivalent constructions do not depart from the spirit and scope of the present disclosure, and various changes, substitutions, and alterations may be made without departing from the spirit and scope of the present disclosure.

What is claimed is:

1. An electronic device, comprising:
   a first region having a first pliability;
   a second region adjacent to the first region, the second region having a second pliability greater than the first pliability;
   an electronic component disposed at the first region;
   a first sensing element disposed at the second region and electrically connected to the electronic component;
   a battery element disposed at the second region; and
   a protection layer encapsulating the battery element and the electronic component,
   wherein the battery element is electrically connected to the electronic component.

2. The electronic device of claim 1, wherein the battery element is closer to a top surface of the protection layer than the electronic component is.

3. The electronic device of claim 1, wherein the protection layer has a lateral surface, and the battery element is closer to the electronic component than to the lateral surface of the protection layer.

4. The electronic device of claim 1, wherein, when the electronic device is worn by a user, the first sensing element is closer to the user's skin than the battery element is.

5. The electronic device of claim 1, further comprising:
a third region having a third pliability greater than the first pliability, wherein the first region is located between the second region and the third region; and
a second sensing element disposed at the third region, wherein, when the electronic device is worn by a user, the first sensing element and the second sensing element are closer to the user's skin than the electronic component is.

6. The electronic device of claim 5, wherein in a cross-sectional view, an imaginary line is defined from the first sensing element to the second sensing element, a central portion of the imaginary line vertically overlaps the electronic component.

7. An electronic device, comprising:
a carrier having a first surface and a second surface opposite to the first surface and defining a cavity through the carrier and exposed by the first surface and the second surface;
an electronic component disposed adjacent to the first surface of the carrier and outside of the cavity; and
a sensing element disposed within the cavity and connected to the electronic component,
wherein the electronic component comprises a microcontroller configured to process a detected biosignal from the sensing element.

8. The electronic device of claim 7, wherein the carrier comprises a conductive element electrically connected to the electronic component, and wherein the sensing element is free from vertically overlapping the conductive element.

9. The electronic device of claim 7, further comprising an underfill disposed between the electronic component and the carrier, wherein the underfill is in contact with the sensing element.

10. The electronic device of claim 9, further comprising a first protection layer disposed within the cavity and in contact with at least three sides of the sensing element.

11. The electronic device of claim 10, wherein the first protection layer is in contact with a bottom surface of the sensing element.

12. The electronic device of claim 10, wherein the underfill is in contact with the first protection layer, and a material of the underfill is different from a material of the first protection layer.

13. The electronic device of claim 7, wherein the sensing element is spaced apart from the carrier.

14. The electronic device of claim 10, further comprising a second protection layer encapsulating the electronic component, wherein a horizontal width of the second protection layer is greater than a horizontal width of the first protection layer.

15. An electronic device, comprising:
a first pliable layer including a top surface, a bottom surface opposite to the top surface, and a cavity penetrating the first pliable layer;
a second pliable layer disposed over the first pliable layer;
a plurality of sensing elements disposed under the bottom surface of the first pliable layer, wherein each of the plurality of sensing elements has a first sensing side; and
an optical component disposed within the cavity and exposed by the top surface and the bottom surface of the first pliable layer, wherein the optical component has a second sensing side,
wherein the first sensing side and the second sensing side face down for sensing.

16. The electronic device of claim 15, wherein a thickness of the optical component is less than a half of a depth of the cavity.

17. The electronic device of claim 15, wherein the plurality of sensing elements are disposed outside of the first pliable layer and the second pliable layer.

18. The electronic device of claim 15, wherein, when the electronic device is worn by a user, the plurality of sensing elements are closer to the user's skin than the optical component is.

19. The electronic device of claim 15, wherein the second sensing side of the optical component is between the top surface and the bottom surface of the first pliable layer.

\* \* \* \* \*